US010333908B2

(12) United States Patent
Buccella et al.

(10) Patent No.: US 10,333,908 B2
(45) Date of Patent: Jun. 25, 2019

(54) TRANSACTION-BASED SECURE INFORMATION DELIVERY AND ASSESSMENT

(71) Applicant: SecuritiNet Inc., Dedham, MA (US)

(72) Inventors: Donato Buccella, Newton, MA (US); Daniel E. Geer, Jr., North Smithfield, RI (US); Patrick Harding, Concord, MA (US); Barry J. Kadets, Waltham, MA (US); Stephen J. MacLellan, Lincoln, MA (US); T. Mark Morley, Dedham, MA (US)

(73) Assignee: SecuritiNet Inc., Dedham, MA (US)

( * ) Notice: Subject to any disclaimer, the term of this patent is extended or adjusted under 35 U.S.C. 154(b) by 142 days.

(21) Appl. No.: 15/013,356

(22) Filed: Feb. 2, 2016

(65) Prior Publication Data

US 2016/0226840 A1 Aug. 4, 2016

Related U.S. Application Data

(60) Provisional application No. 62/111,359, filed on Feb. 3, 2015.

(51) Int. Cl.
*H04L 29/06* (2006.01)

(52) U.S. Cl.
CPC ........ *H04L 63/0435* (2013.01); *H04L 63/067* (2013.01); *H04L 63/0876* (2013.01); *H04L 63/123* (2013.01)

(58) Field of Classification Search
CPC .............. H04L 63/0435; H04L 63/067; H04L 63/0876; H04L 63/123
See application file for complete search history.

(56) References Cited

U.S. PATENT DOCUMENTS

| 7,706,540 | B2 | 4/2010 | Fransdonk |
| 8,737,624 | B2 | 5/2014 | Selgas et al. |
| 8,751,793 | B2* | 6/2014 | Ginter .................... G06F 21/10 380/255 |
| 8,812,702 | B2 | 8/2014 | Mendez et al. |
| 9,026,805 | B2 | 5/2015 | Acar et al. |
| 9,258,117 | B1 | 2/2016 | Roth et al. |
| 9,311,500 | B2 | 4/2016 | Roth et al. |
| 2003/0161473 | A1 | 8/2003 | Fransdonk |
| 2003/0161476 | A1 | 8/2003 | Fransdonk |
| 2006/0193474 | A1 | 8/2006 | Fransdonk |
| 2006/0210084 | A1 | 9/2006 | Fransdonk |
| 2007/0185878 | A1* | 8/2007 | Fierstein ................. G06F 21/10 |
| 2007/0258437 | A1* | 11/2007 | Bennett ............... H04L 63/1441 370/352 |

(Continued)

FOREIGN PATENT DOCUMENTS

EP 2 472 430 A1 7/2012

*Primary Examiner* — Joseph P Hirl
*Assistant Examiner* — Sayed Aresh Beheshti Shirazi
(74) *Attorney, Agent, or Firm* — VLP Law Group LLP

(57) ABSTRACT

This patent is generally directed to a transaction-based secure information delivery system and method referred to as "SEDS" herein. SEDS consists of secure method(s) and infrastructure to transmit sensitive information, such as but not limited to medical information. SEDS may be used instead of email, fax, removable media and other non-secure methods. SEDS also supports a sender/receiver risk-assessment based communication protocol.

5 Claims, 7 Drawing Sheets

(56) References Cited

U.S. PATENT DOCUMENTS

| | | | |
|---|---|---|---|
| 2008/0008125 A1* | 1/2008 | Pham | H04W 4/50 |
| | | | 370/329 |
| 2009/0006202 A1* | 1/2009 | Alroy | G06Q 30/0269 |
| | | | 705/14.66 |
| 2012/0144198 A1* | 6/2012 | Har | H04L 63/0869 |
| | | | 713/170 |
| 2013/0212704 A1 | 8/2013 | Shablygin et al. | |
| 2013/0287204 A1 | 10/2013 | Davis et al. | |
| 2013/0290700 A1 | 10/2013 | Davis et al. | |
| 2016/0127895 A1 | 5/2016 | Bangole et al. | |
| 2016/0132874 A1 | 5/2016 | Carrott | |
| 2016/0132877 A1 | 5/2016 | Carrott | |
| 2016/0171492 A1 | 6/2016 | Carrott | |
| 2017/0200137 A1* | 7/2017 | Vilmont | G06Q 20/10 |

\* cited by examiner

TRANSACTION-BASED SECURE INFORMATION DELIVERY AND ASSESSMENT

CROSS-REFERENCE TO RELATED APPLICATIONS

The present application claims the benefit of U.S. Provisional Patent Application Ser. No. 62/111,359 which was filed on Feb. 3, 2015 by Donato Buccella et al. for TRANSACTION-BASED SECURE INFORMATION DELIVERY AND ASSESSMENT, which is hereby incorporated by reference.

BACKGROUND

This patent application is directed to a transaction-based secure information delivery system and method.

SUMMARY

The techniques described herein may be used to provide a Secure Electronic Document Service (SEDS) message communication system that consists of secure method(s) and infrastructure to transmit sensitive information, such as but not limited to medical information, financial records, trade secret information, sensitive documents, commands, and other critical communications between electronic devices. SEDS may be used instead of email, fax, removable media and other less secure methods.

SEDS has several attributes, including a transaction based encrypted messaging protocol, and sender/receiver risk-assessment controls on the protocol.

More particularly, in one embodiment, a transaction-based method for delivery of sensitive information first verifies or authenticates an identity of a sender. A request message is sent from a Secure Network Client (SNC) device to a secure network backend (SNB) causing a message waiting notification message to be sent to an SNC device at a receiver. After verifying and/or authenticating an identity of the receiver, the method assesses additional risk aspects of the receiver's security rating, and if these match a predetermined rating criteria of the sender, a message can be exchanged.

In some implementations, when a message is to be exchanged, the message payload is symmetrically encrypted with a unique randomly generated key and initialization vector (IV) such that if one key is compromised only one message is revealed. The symmetric encryption is performed in the sender side SNC and forwarded to the SNB located in a network location such as at a cloud location. The encrypted message is received at the cloud side SNB with the key, and the IV. The SNB will send the notification message in encrypted format. The receiver SNC needs the user password in order to extract the IV from the notification message. The SNC only stores the encrypted message and the key and does not further store the IV.

DETAILED DESCRIPTION

Introduction

Figure 1:
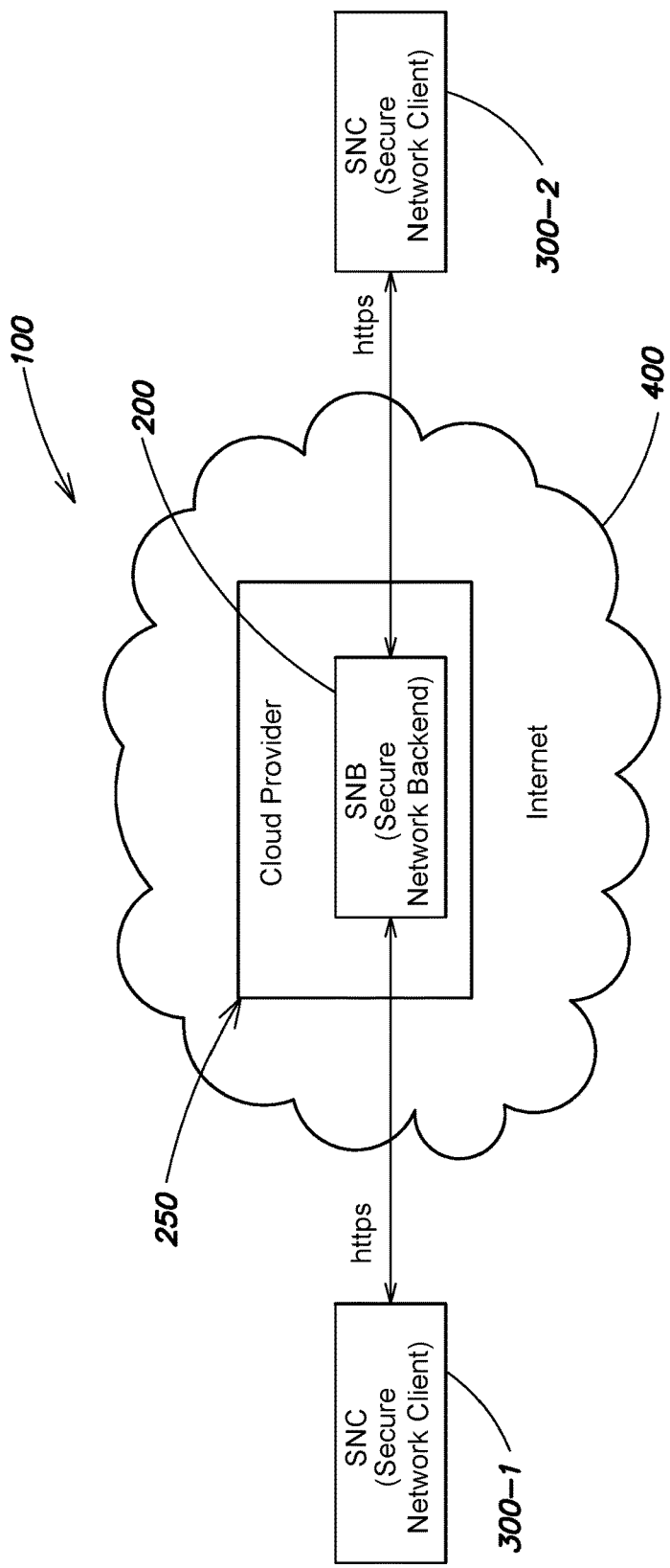
FIG. 1 illustrates a high level topology of the Secure Electronic Document Service (SEDS).

In one embodiment of the Secure Electronic Document Service (SEDS) messaging system and methods, the sensitive information exchanged includes medical information such as Electronic Health Records (EHR). However it should be understood that other types of documents that include medical information such as medical history (Personal Health Records) and other patient medical information may be exchanged.

In such a medical application, typical users may include Medical Practitioners, Healthcare Delivery Systems, Insurance Companies, Providers (Labs, Radiology, etc.), Patients, or Medical Devices.

More generally, SEDS may be used for sending and receiving messages that contain any type of sensitive information, such as financial records, competitive business information, trade secrets, strategic military information, classified documents, text messages, commands and data to control remote sensors and devices, and the like. SEDS may enable messages to be exchanged between many different types of data processors such as computers, desktops, laptops, servers, network appliances, smart phones, tablets, and the like. SEDS may also be used to connect other things, such as physical objects, devices, vehicles, buildings and other items which are embedded with electronics, software, sensors, and network connectivity, which enables these objects to collect and exchange data (commonly referred to as Internet of Things (IoT) connected devices). SEDS may feature a number of transactions that can be executed between SEDS registered users, and in some cases unregistered users, related to sending and receiving messages that contain sensitive information.

Users/Device Registration and Verification

SEDS users and/or their devices typically go through a registration process and varying levels of identity verification depending on the level of trust and transaction features desired. (It should be understood that while the term "user" refers to a sender or receiver of a message herein, that both computers sending documents and other information as well as other connected objects (such as IoT devices) can utilize SEDS).

Senders typically need to have completed at least a basic identity verification process before they can send sensitive information (see the example Sender/Receiver access rights matrix discussed below in connection with FIG. 8.)

Senders can typically send to unregistered users. Unregistered users typically need to register before being able to open any sent content, unless the Sender vouches for and assumes responsibility for the unregistered receiver Users may be identified by a valid business email address. In a preferred implementation, free email services (Gmail, Yahoo, etc.) will not be accepted for this purpose.

The system should be able to support user levels or tiers based on both service and access levels.

In addition to individual users, groups of users may also be supported as a transaction participant; however it may be desirable to not allow nesting of user groups.

A process can be provided for identifying and registering physical devices. Such a process, for example, may be coordinated with the device manufacturer.

In one simple implementation, users create an SEDS password. In other implementations, SEDS may support integration of internal customer single-sign on systems for authentication.

Transactions and Data

The following are some desirable, but not necessarily required, attributes of the transactions and data used in SEDS.

Transactions in the system should have states that can be tracked in real time i.e. SENT, RECEIVED, OPENED, etc.

Transactions can expire if actions not taken within specified period (i.e. message not opened within specified time frame).

Transaction states and actions generate notifications to transactions participants (i.e. texts or email).

One simpler initial implementation of SEDS may not open (examine or transform) the secure information being transmitted in a transaction. As far as SEDS is concerned the secure information is an opaque blob of data that needs to be secured and moved.

SEDS stores the secured information (blob) only in encrypted from and only during message transition. It does not store any secure information (blob) in the clear.

Information is secured at the Sender's and Receiver's locations or systems. Any data traversing SEDS will not be viewable by SEDS.

One of the key features is to protect against man-in-the-middle attack.

In order to protect against a rogue SEDS worker additional attributes may include:

Split key technologies

Hardware Security Modules (HSM) at customer sites

Users may enter both required (by SEDS) and optional (by the user) metadata for each transaction. The entered metadata is accessible by SEDS and might be used for audit trail and for analytics (after it is normalized and de-identified).

All transactions have a detailed audit trail that can be retrieved in real time by the transaction participants (depending on the semantics of the specific transaction).

The logs may be immutable (for non-repudiation) and their access controlled.

Other Assumptions and Constraints

SEDS is preferably implemented as a cloud based Software-as-a-Service ("SaaS") application that runs in a redundant, suitable cloud provider(s). For example, in a medical records application, the cloud provider should be Health Insurance Portability and Accountability Act (HIPAA) compliant. The cloud component is referred as the SEDS "backend".

SEDS's backend should store a user's profile information and authentication credentials, temporary transaction information while a transaction is active (sender, receiver(s), key material identifiers, etc.), de-identified transaction metadata, transaction audit trail, and billing information.

SEDS software components also reside at the edges of the transaction close to the users and are called the SEDS "clients". These can consist of application servers (referred to gateways) and/or other client components such as fat desktop clients and native tablet/smart phone applications.

All accesses to SEDS including administrative and maintenance tasks are preferably logged. In some implementations SEDS may implement geo-fencing functionality in order to limit/control access from specific locations.

Design Goals

Some additional desirable (although not necessarily required) attributes of SEDS include: Stateless operation between the Secure Network Service Backend (SNB) and the Secure Network Service Client (SNC).

The SNC component is implemented as a "wrapper" around an SEDS Application Program Interface ("API"). In example implementations, the SNC may be a standalone internal web application, a fat client desktop application, a native mobile application running on a phone and tablet, or an integrated module within an Electronic Health Records (EHR) system.

Access and communication to the SNB is preferably only possible through the SEDS API.

The SEDS API consists of an Remote Procedure Call ("RPC") layer implemented using web services (and other technologies like JavaScript Object Notation ("JSON"), Representational State Transfer ("REST"), etc.) and a local cryptography layer used to handle message payload encode/decode operations.

SEDS uses a message/action queue model where transactions are posted and users are notified. The user then takes action using the SNC to retrieve messages, etc.

Notifications can be a combination of email messages, texts (or direct Tweets).

The SNC periodically communicates with the SNB when active. This communication is used for housekeeping, recovery and key rotation. This is preferably part of the API so integrators do not have to implement it.

The SNB also implements all functionality related to user registration and verification. There are both API components and Internet facing portal for users to use for these purposes.

The SNB also implements the notification systems.

System Topology

FIG. 1 is a high level diagram of one possible embodiment of the Secure Electronic Document Service (SEDS) system and/or methods 100. It includes the Secure Network Backend (SNB) 200 and Secure Network Client (SNC) 300 components mentioned above. There are at least two SNC components 300-1, 300-2, namely a sender and receiver for a typical transaction, although most systems 100 may have many SNCs 300 active at any one time. The SNB 200 and SNCs 300 are connected via a communication network such as the Internet 400.

SNB 200 runs in a private or public cloud service provider 250 capable of providing sufficient levels of security. For example, in an Electronic Health Records (HER) application, the SNB should be rated for handling HIPAA data.

SNB 200 also preferably has high availability ("HA") within the cloud provider 250; and in some implementations the SNB is implemented with redundant cloud provider(s).

SNC 300 uses an underlying secure protocol for communication with the SNB 200 such as https. All communications are Remote Procedure (RPC) calls using either web services such as Simple Object Access Protocol (SOAP), Representational State Transfer (REST) or any other implemented RPC transport. There should be no other communications permitted between the SNC 300 and the SNB 200.

SNB High-Level Architecture

Figure 2:
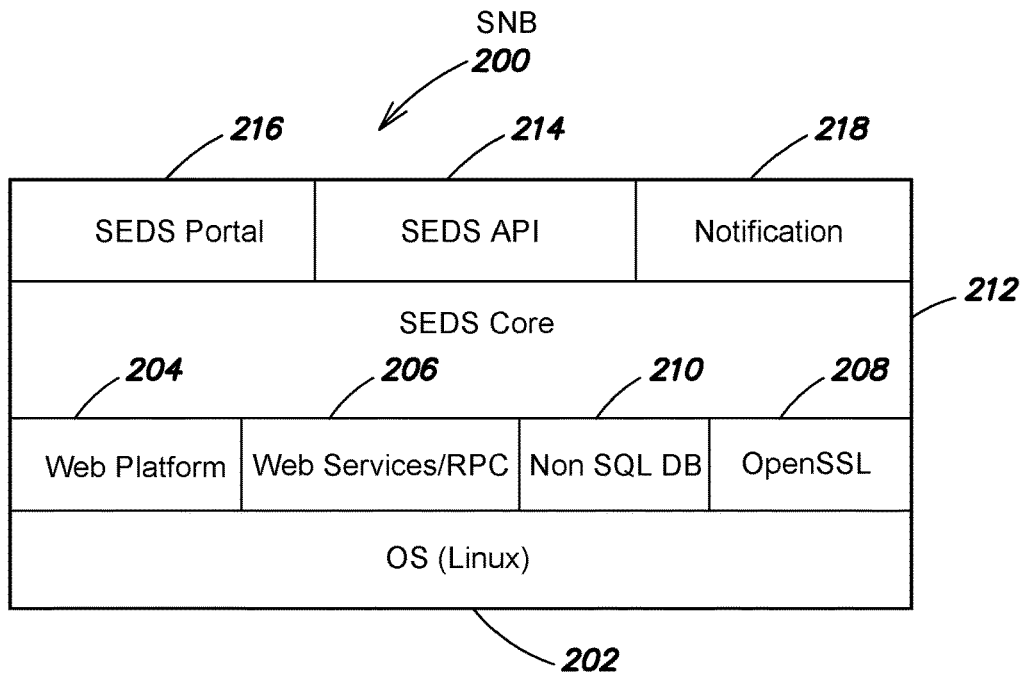
FIG. 2 is a high level architecture of the Secure Network Backend (SNB).

FIG. 2 is a high level architecture diagram of the SNB 200. It includes a number of functional layers including an Operating System (OS) 202, web platform 204, web services/RPC 206, OpenSSL 208, non-SQL database 210, SEDS core 212, SEDS API 214, SEDS portal 216, and Notification 218.

OS 202

Linux is the preferred choice for many reasons including cost, access to resources and providers. Code and dependencies should be user-mode to reduce Linux version issues and to support multiple providers.

Web Platform 204

This is a high performance, high availability capable http server layer. All access to SNB 200 goes through this layer. There are many public cloud-based implementation choices possible for this platform including Amazon Web Services, Rackspace, Google Cloud, Microsoft Cloud, and/or private cloud platforms available from Oracle, Hewlett Packard, and other vendors.

Web Services/RPC 206

This is the layer that implements the remote call handling and marshaling of the input and output. There are number of choices available and these are chosen based on the web platform and the toolset in use.

OpenSSL 208

This is the cryptography layer. Heartbleed (a security bug in Open SSL) notwithstanding, this is preferred as it is a multi-platform choice.

Non SQL DB 210

This is a non-Structured Query Language, robust data store.

SEDS Core 212

Essentially this is the business logic for SEDS. All transactions, cryptography protocols, logging/auditing and all other supporting functions are implemented in this layer. It is described in more detail below.

SEDS API 214

This is the server side handler/wrapper for the API calls coming from the SEDS API.

SEDS Portal 216

This is an Internet facing web application that the SEDS end users and customers see. Users use it to register, verify themselves, profile management (password change, etc.) check their own transaction status and possibly even to initiate transactions. Customers may also use this to bulk register users, set user access level, create groups, browse logs, and overall customer profile management.

Notification 218

This layer is used to send notification messages for all transaction and user events.

SNC High-Level Architecture

Figure 3:
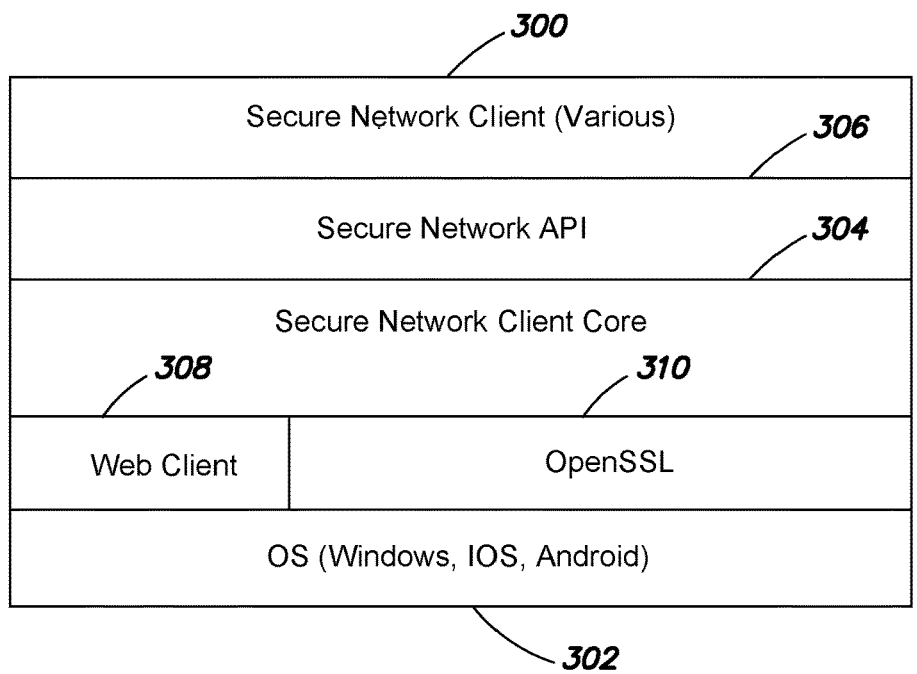
FIG. 3 is a high level architecture of the Secure Network Client (SNC).

FIG. 3 is a high level functional layer diagram for the SNC 300.

OS 302

The client 300 is typically multi-platform (actually the API is multi-platform). Commonly used Operating Systems (OS) such as Windows, OSX, IOS (both iPhone and iPad) and Android are the most likely platforms. The Web Client layer 308 is provided by the OS and/or browser.

SEDS Client Core 304

This layer implements the local API calls (local cryptography for encoding/decoding) and all necessary service for the API to work in the client 300.

SEDS API 306

This is the "caller" wrapper for the API. This is a multi-platform module and it is provided in binary form.

SEDS Client 308

This is the user interface for the user, typically web-based. The system can provide a smartphone, tablet version and/or an intranet web based version.

Open SSL 310

This is the network cryptography layer corresponding to the OpenSSL layer 208 in the SNB.

High-Level Transaction Sequences

Figure 4:
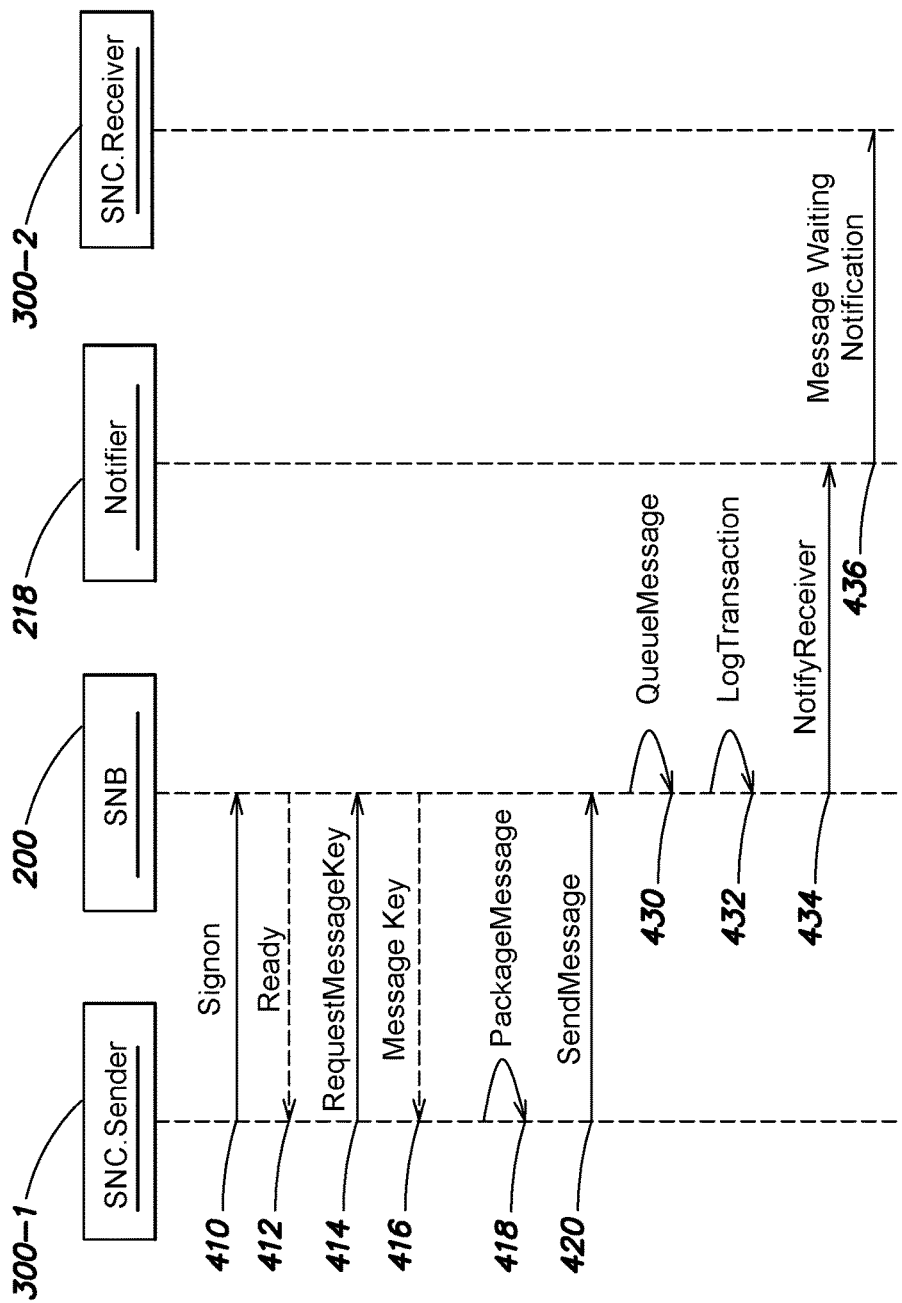
FIG. 4 is a high level message send sequence diagram.
Figure 5:
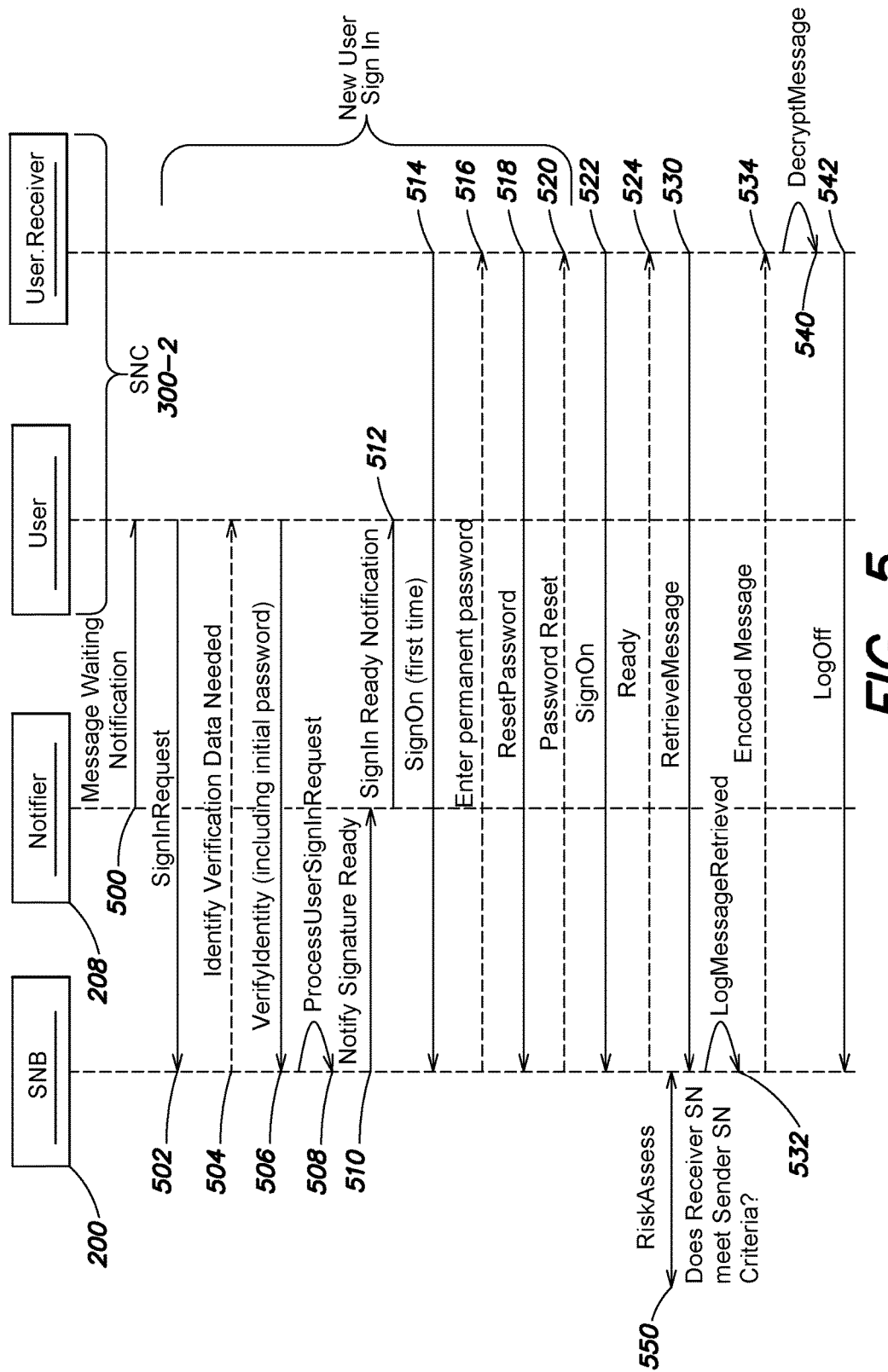
FIG. 5 is a high level retrieve message sequence diagram.

FIG. 4 is a high level Message Send Sequence Diagram used on the Sender side and FIG. 5 is a high level Retrieve Message Sequence Diagram used on the Receiver side.

Before discussing these protocol diagrams in detail some initial operations and assumptions are discussed.

Message Transfer Protocol

The transfer operations are carried out by API calls. As mentioned above, the system 100 use a connectionless/stateless RPC mechanism such as REST or JSON-RPC. The following description uses REST as one example, but the same concepts can be implemented using other RPC models.

Message Authentication

Although not shown in detail in the protocol diagrams, for the REST version of these API calls, one can use the same message authentication approach used by Amazon S3 API (see http://docs.aws.amazon.com/AmazonS3/latest/dev/RESTAuthentication.html).

The basic concept is:

Every user has a unique username and password shared with the service side (in our case the SNB)

For each Hypertext Transfer Protocol ("HTTP") REST call whether it is a GET, POST, PUT, (each a REST verb) etc. the caller/sender adds an HTTP header to the request with a message authenticator value Hash Message Authentication Code ("HMAC"). The value is calculated by hashing (using a cryptographic secure hash algorithm like SHA-1) a stream of bytes containing the username, password and message specific values such as the date, the request Uniform Resource Locator ("URL"), call parameters and request body.

The request components (stream of bytes) used for authentication are hashed together in a very specific order using formats and encodings that have been previously agreed to on a per request basis. In other words, a given request "A" elements used for the HMAC can be different than for another request "B". This is because different requests have different elements and parameters and it is hard to be uniform. In our case we will try to be as consistent as possible without compromising security.

This approach provides both user authentication and content integrity. The system should require HTTPs for all REST API calls.

Other Assumptions/Glossary

The SNB 200 has a third party verifiable certificate. For management purposes it should be different than the certificate used for https on the web farm. We will call the SNB keys Sp (public key) and Sv (private key).

When the user installs the SNC application on their device or accesses the local SNC web application for the first time it receives a certificate for the SNC with the SNB public key (only).

The user has a username Un and a password Up.

For asymmetric encryption RSA keys not smaller than 2048 bytes are preferable.

For symmetric encryption AES-256 is preferably used.

For cryptographic hashing SHA256 is preferably used although SHA1 is also possible.

All messages are binary byte streams are formatted in network byte order.

In the diagrams, curly braces { } are used to denote asymmetric encryption. For example, Sp{Up} means that the user password Up is asymmetrically encrypted with the SNC public key Sp.

Square brackets [ ] denote symmetric encryption. For example Mk[EHR Blob] means that an EHR data blob is encrypted with a symmetric key Mk.

SHA( ) denotes hashing. For example SHA(EHR Blob) means a cryptographic hash of EHR data blob.

In the diagrams, TS stands for a timestamp and RCPT stands for message recipient.

Message format specifics like field order, length and padding are omitted for simplicity and are not critical.

Turning attention to FIG. 4, a Sender side SNC 300-1 uses SNB 200 to send information securely to a Receiver side SNC 300-2. A Signon message 410 and Ready reply 412 are exchanged between SNC 300-1 and SNB 200 to authorize communication on the Sender side. It should be understood that at this point the Sender may already also be authenticated as explained above or in some other appropriate way. A MessageKey is requested 414 and received 416. Next, the message is Packaged 418 and sent at a SendMessage step 420 to SNB 300.

At the SNB 300, the received message is queued at QueueMessage 430 and a new transaction is logged at 432. A NotifyReceiver step 434 (such as may originate from Notifier layer 218) causes a MessageWaiting notice 436 to be sent to the SNC receiver side 300-2.

FIG. 5 is a high level illustration of the further process for completing the transaction with the receiver side SNC 300-2. A MessageWaitingNotification 500 is sent to the receiver SNC 300-2. SignonRequest 502 at the receiver side then occurs.

Processing at this point for a new user may involve identity verification (such as with passwords) in steps 504 and 506. The new receiver user signon request is then processed in step 508. If the receiver is approved for communication with the sender, then a Signin ready 510 is returned from the SNB 200 through the notifier 208 to the SNC receiver 300-2 at step 512. Optional steps 514, 516, 518, and 520 allow for password setting and resetting.

Signon for an existing user is processed beginning at step 522 and a ready state is reached at 524. At this point message delivery may also involve a RiskAssessment 550 as described in more detail below in connection with FIG. 8.

At Step 530 the received side can request RetrieveMessage, and after a log step 532, the encoded message may be sent 534 from SNB to SNC 300-2. In step 540 the message is decrypted and logoff occurs at 542.

DETAILED MESSAGE SEND AND RECEIVE PROCESSING

Figure 6:
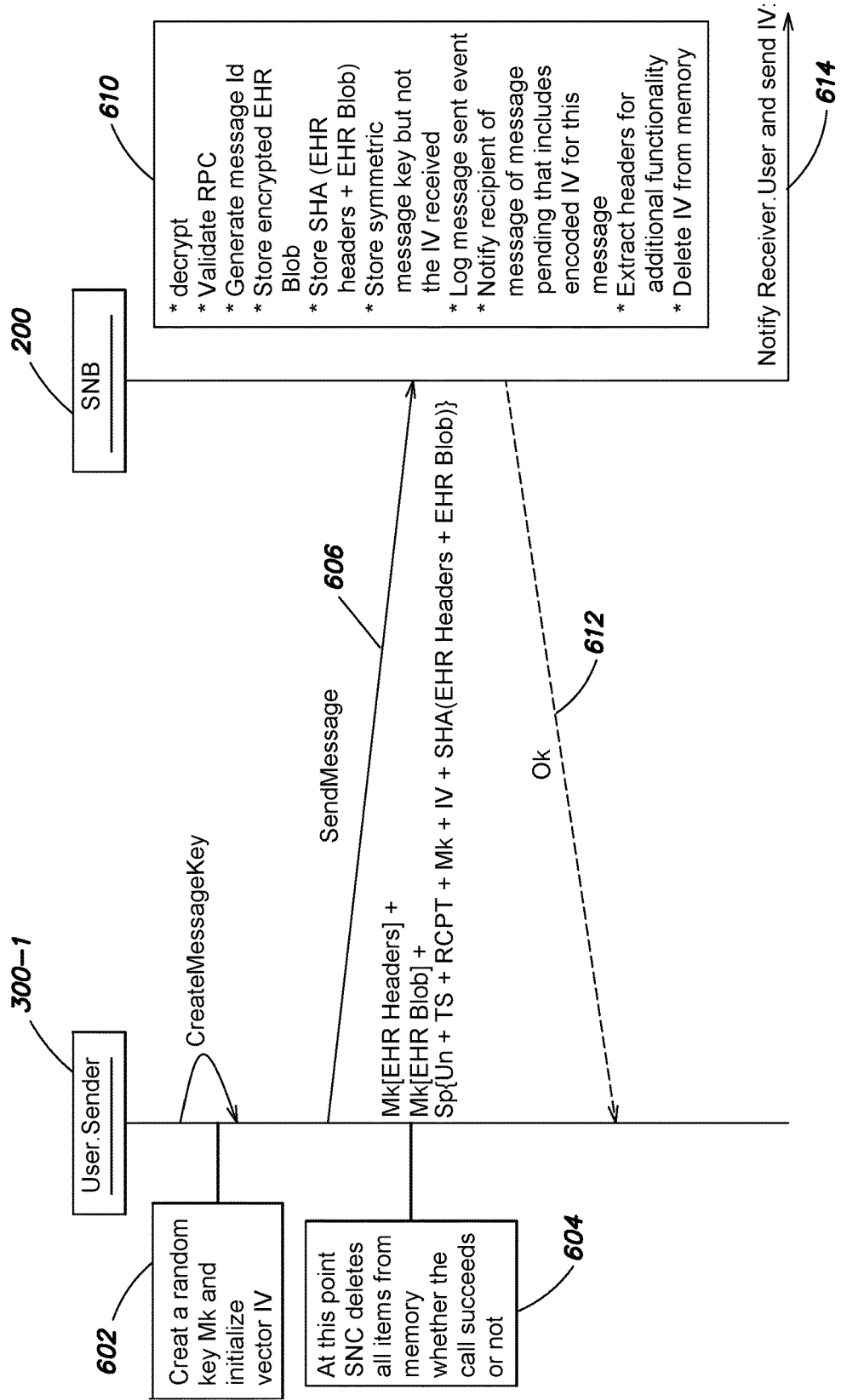
FIG. 6 is a more detailed message send process.
Figure 7:
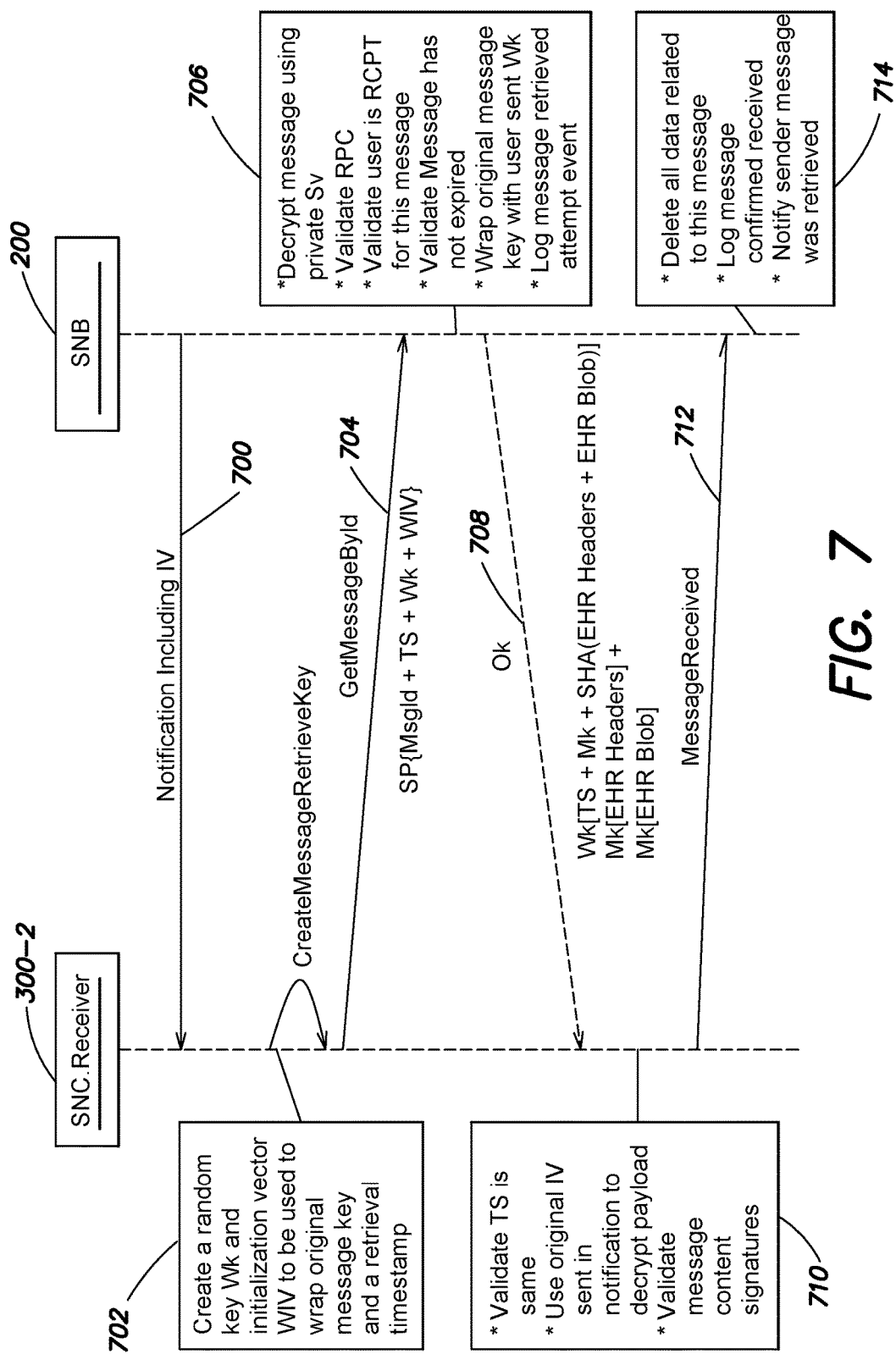
FIG. 7 is a more detailed message receive process.

FIG. 6 is a detailed Message Send Process and FIG. 7 is a detailed Message Receive Process.
Send/Receive Protocol Summary As mentioned above briefly, the sender and receiver are authenticated and verified before message exchange.

Once verified, the send process in FIG. 6 can commence. In an initial step 602, to enable every message payload to be symmetrically encrypted, a unique, randomly generated symmetric MessageKey (Mk) and Initialization Vector (IV) are created by the SNC 300-1. This is in accordance with the principle of Perfect Forward Security where if one key is compromised only one message is revealed.

The message is then encrypted on the sender SNC 300-1 in step 606 according to the expressions:

$$Mk[Headers]+Mk[Blob]+Sp\{Un+TS+RCPT+Mk+IV+SHA(Headers+Blob)\}$$

While the Figures mention EHR Headers and EHR Blob, it should be understood that information other than Electronic Health Records can be secured using these techniques; and while the system is referred to herein as the Secure Electronic Document System, it should be understood that the Blob may represent an electronic document, or only a portion thereof, or other types of data such as a database record, a control command, or indeed any digital data that may or may not represent a human-readable message. It should also be understood that the Headers may or may not be present, depending upon the type of data being sent.

The Headers portion of each message, if present, will depend upon some agreed to format. It may include things such as a sender ID, receiver ID, IP addresses, document name, document type, timestamp, date and time, transaction ID, sequence numbers, message size, message hash, key words, or XML defining these or other fields. It may also depend on the specific API in use or industry requirements as well. The header information may be used to establish the log record of the data flow, including signing information for operational and non-reproduction purposes. The header may include clear text or still further encrypted information. The header may be delivered to an external block chain service.

The symmetric encryption step is always performed in the sender side (SNC 300-1).

At step 604 the SNC 300-1 deletes all items from memory whether the call succeeds or not At step 610 the cloud side (SNB 200) decrypts the Message section originally encrypted by Sp using its private key (Sv). The decrypted section contains message decryption key(s) and a crypto-signature used to validate the encrypted blob, SendMessage using the public key (Sp) and the Message Key (Mk). As shown in the drawing, the SNB 200 performs several steps at this point. The RPC for the sender is validated to ensure that the message is well formed and valid (for example, that the content of the header is correct for the use, checksums match, and so forth), and a message ID is generated. The SNB 200 then stores the encrypted Blob, SHA(Headers+Blob) and the symmetric message key Mk. However the IV is not stored, and is explicitly deleted from memory. A message sent event is then logged and acknowledgement 612 is sent back to the SNC 300-1.

In step 614 the intended receiver SNC 300-2 is notified of a pending message; the notification will include the IV associated with the transaction and a message identifier. The SNB 200 then deletes the IV from its local memory. At this point or in step 610 the SNB 200 may also extract message headers to provide other functions. In one example, since the SNB 200 does not save the message content itself and only the headers, the header content may be extracted, for the purpose of log information (sender, receiver, timstamps, etc.) or operational analytics, security audits and the like.

Turning now to FIG. 7 more particularly, in state 700 the SNB 200 sends the IV and Msg ID (encoded by encrypting it with the recipient user password) to the SNC 300-2 on the receiver side as a notification message telling the receiver that there is a message pending. As mentioned above, once the notification message is sent in state 700, the SNB 200 only stores the encrypted message and the key and "forgets" the IV. The net result is that SNB 200 cannot decrypt the message at any point going forward.

Notification messages can be transmitted in step 700 via in convenient way, including email, Short Message Service ("SMS") (texts), Twitter or any messaging platform.

The recipient SNB 300-2 extracts IV and Msg ID from the notification message (and stores these in a key store if needed).

When the receiver is ready to retrieve the message, the encrypted message along with the original key is downloaded from the SNB 200 to the receiver SNC 300-2. This is accomplished with a series of detailed steps to provide extra security. For example, the key is encrypted with a locally generated key wrap symmetric key.

In the example shown, at step 702 the receiver side SNC 300-2 creates a MessageRetrieveKey including a random symmetric key Wk and its own initialization vector WIV to be used to wrap the original message key and a retrieval timestamp. In step 704 the receiver SNC sends an encrypted message to SNB 200 with this information as:

Sp{MsgId+TS+Wk+WIV}

At step 706 the SNB 200 performs a couple of steps. The SNB decrypts the message using private key Sv. The RPC for the receiver is validated, and it is confirmed that the message has not expired (which may be determined from the timestamp). The original message is then wrapped with the receiver user generated key, Wk and the message is logged.

The encrypted payload is sent at step 708 as

Wk[TS+Mk+SHA(Headers+Blob)]

Mk[Headers]+

30Mk[Blob]

In step 710, decryption is performed locally in the SNC. Validation of the message (for example, what was encrypted by Sp in the sent message) may then allow the receiver client to validate that the message received was indeed the message sent and not modified. In order to decrypt the message the receiver uses the encoded IV that they received in the notification message in step 700. At this point the receiver has all that is needed to decrypt the message. Valid message content may also be verified with message content signatures.

In step 712 the SNC 300-2 confirms receipt of the message to the SNB; in turn the SNB at step 714 can delete all data related to the message, log that the message receipt was confirmed, and notify the sender of completion.

Additional Notes

The SNB 200 cannot decrypt the original message payload because it only momentarily keeps the initialization vector used to encrypt the message. The recipient receives the IV (in a specially encrypted form) in a notification message.

This message specific IV is encrypted using an SNC key and message specific information (such as an ID, sequence number or other information unique to the message).

Message information is stored in a database 210 in the SNB 200. All sensitive information, like the message key and the usernames, are encrypted using a symmetric master key held in the SNB 200 server (preferably in an Hardware Security Module ("HSM") device). The sensitive information is symmetrically encrypted with the before mentioned server master key before it is written to the database 210.

The approach above requires no Rivest-Shamir-Adleman ("RSA") key pairs for the client SNC to operate. This is a management advantage. Requiring client certificates being distributed and managed by the infrastructure it is cumbersome and error prone. Requiring strong passwords and periodic password changes is a better method.

Ad hoc Document Centric Secure Business Collaboration—Further Aspects

A. Independent Centralized Message Exchange
 1. User Authentication
 2. User Authorization
 3. User Identity Verification
B. Secure Transactions
 1. Message/Document Based Transactions
  a. Send with Receipt Verification
  b. Send with Approval/Signature Required
  c. Reject Message Transaction
  d. Request Information
C. Full Life-cycle Data Protection
 1. Data is protected at rest and in motion at all times
 2. Split-Key Operation
  a. Only receiver has all key material needed to decrypt message
  b. Message Exchange temporarily stores encrypted messages (that it does not know how to decrypt) until they are delivered
  c. Message Exchange does not store delivered messages Risk Assessment Protocol SEDS 100 also supports a multi-tiered, multi-dimensional, mathematically-driven location security rating/assessment system, using self attested, external third party confirmed data and proprietary algorithms to develop a location security rating/assessment and updated using new external and real time information proprietarily blended algorithmically, together with proprietary heuristic modeling of security risk of the location.

Using the assessment protocol, a Sender can decide to:
1. Not send a message based on an assessment of the Receiver
2. Perform/require additional confirmatory security procedures prior to sending
3. Send based on a prior long-term working relationship with the Receiver, or other data known to the Sender FIG. 8 illustrates an example risk assessment. Each user is given a SEDS risk score referred to as their SN score herein. The SN risk score is based on a number of factors including:

Physical Security—rates the building, organization, other attributes of the physical environment IT Security—rates the processors, operating systems, firewalls, networks, storage systems, cloud providers, and other aspects of the Information Technology in use EHR Application—rates the Electronic Health Record software application being used Personnel—rates the risk of disclosing information to the individual person The Risk Assessment function of the SNB obtains a rating for each of the four factors and develop an overall assessment for each user as a Sender or Receiver. This may occur in the detailed protocol process of FIG. 5 at step 550, but may occur at other stages in that specific protocol. The Risk Assessment function may also be used with protocols other than those described in FIGS. 4 through 7.

Figure 8:
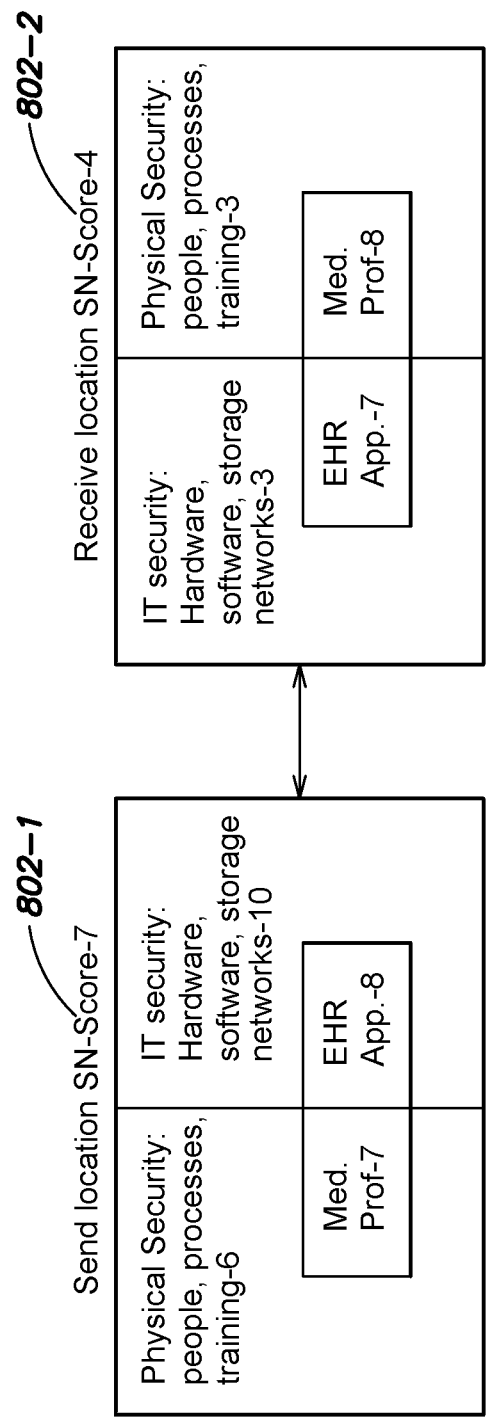
FIG. 8 illustrates an example message risk assessment.

In the example shown in FIG. 8, the Sender has an overall SN score of 7 and the Receiver a SN score of 4. These were arrived at by computing a score 802-1 on the Sender side taking into account the four scores (Physical Security, people, processes and training of 6), IT Security, Hardware, software and storage networks used rating of 10, that the user is a Medical Professional (such as a particular hospital) rated at 7, and that the particular EHR application in use is rated at 8, giving an over all blended score 802-1 of 7. A similar blended score 802-2 of 4 is determined for the receiver side for the four attributes.

The assessments may originate in various ways, by self-assessment by the Receiver and Sender or by ratings assigned by the SEDS service provider, or some third party rating service. Personnel assessment may be through scoring the answers to an on-line questionnaire completed by or for the person. IT assessment may be via questionnaire completed by the user's IT staff or verified via an on-site visit. Physical security may also be via questionnaires with on-site verification. EHR ratings would be typically assessed by the SN service provider ranking the various levels of safety associated with different software applications in use. Answers can be verified via on-line databases.

The Risk Assessment function is typically implemented in the SNB 200 (cloud/server) as part of the Send or Receive process described above in FIG. 4 and/or FIG. 5.

In one implementation, a Sender-member can choose to use the SN scores in one of two ways:

1. Receiver-with an SN-Blended Score
2. Receiver-without an SN-Score

In a transaction type 1, the Sender can set a threshold for the minimum acceptable Blended Score. Any proposed transaction with a Receiver having a lower score will not be completed by the SNB, and the EHR will not be delivered. The threshold can be enforced by the SNB maintain this preference information for each Sender.

In a transaction type 2, where no SN Score is available at the SNB for a particular receiver, the Sender may alternatively assume all responsibility for the transaction, except the secure transport.

When a transaction type 2 occurs, the components of the endpoint/Receiver can be solicited to join the SEDS and get their own SN-score.

Initial SN Ratings (sub-scores of components of the SN-Score) will be determined from questionnaires and tested via on-line databases.

Higher available subsequent SN-Ratings will be dependent, on additional confirmations, certificates, audits, etc.

Initial ratings and downgrades can be automated. Upgrades can be semi-automated.

The invention claimed is:

1. A method for delivery of sensitive information using transactions, the method comprising:
   verifying and/or authenticating an identity of a sender;
   sending a request message from the sender to a secure network backend (SNB) causing a notification message to be sent to a receiver;
   verifying and/or authenticating an identity of the receiver;
   when additional aspects of a security rating for the receiver match a predetermined rating criteria of the sender, performing additional steps of:
   encrypting the sensitive information;
   sending the sensitive information as a message payload to the receiver; and further
   generating an encrypted message by symmetrically encrypting the message payload with a unique randomly generated key and initialization vector (IV), such that the unique randomly generated key is compromised only when the message payload is revealed;
   wherein the step of generating the encrypted message is performed in a sender side client (SNC);
   receiving the encrypted message at the SNB with the unique randomly generated key and the IV;
   sending, by the SNC, the IV encoded by encrypting it with a sender user password within the notification message; and
   only storing the encrypted message and the unique randomly generated key at the SNC and not further storing the IV.

2. The method of claim 1 wherein the step of verifying and/or authenticating an identity of a sender is via an email address.

3. The method of claim 1 wherein the step of verifying and/or authenticating an identity of a receiver is via an email address.

4. The method of claim 1 additionally comprising:
   assigning groups of senders and receivers as transaction participants.

5. The method of claim 4 additionally comprising:
   determining a Blended Score that depends on the security rating of the receiver and the predetermined rating criteria of the sender; and
   not delivering a message to transaction participants that have a Blended Score lower than a minimum acceptable Blended Score.

* * * * *